United States Patent
Cooney, III et al.

(10) Patent No.: US 8,206,453 B2
(45) Date of Patent: **\*Jun. 26, 2012**

(54) SIGMOID NOTCH IMPLANT

(75) Inventors: William Cooney, III, Rochester, MN (US); David Leibel, Princeton, MN (US); Richard Berger, Rochester, MN (US)

(73) Assignee: Mayo Foundation for Medical Research and Education, Rochester, MN (US)

( \* ) Notice: Subject to any disclaimer, the term of this patent is extended or adjusted under 35 U.S.C. 154(b) by 1461 days.

This patent is subject to a terminal disclaimer.

(21) Appl. No.: 11/605,052

(22) Filed: Nov. 27, 2006

(65) Prior Publication Data

US 2007/0142919 A1     Jun. 21, 2007

Related U.S. Application Data

(63) Continuation of application No. 11/001,572, filed on Dec. 1, 2004, now Pat. No. 7,160,331.

(51) Int. Cl.
*A61F 2/42* (2006.01)

(52) U.S. Cl. .................................................. 623/21.12

(58) Field of Classification Search .... 623/20.11–20.13, 623/21.11–21.19, 19.11–19.14, 20.15, 20.18–20.2, 623/14.12, 20.32–20.34
See application file for complete search history.

(56) References Cited

U.S. PATENT DOCUMENTS

| | | |
|---|---|---|
| 3,714,940 A | 2/1973 | Palmer |
| 4,008,495 A | 2/1977 | Cavendish et al. |
| 4,280,231 A | 7/1981 | Swanson |
| 4,538,305 A | 9/1985 | Engelbrecht et al. |
| 4,645,505 A | 2/1987 | Swanson |
| 4,936,854 A | 6/1990 | Swanson |
| 5,080,673 A * | 1/1992 | Burkhead et al. .......... 623/19.11 |
| 5,108,444 A | 4/1992 | Branemark |
| 5,133,762 A | 7/1992 | Branemark |
| 5,314,485 A | 5/1994 | Judet |
| 5,405,400 A | 4/1995 | Linscheid et al. |
| 5,458,646 A | 10/1995 | Giachino et al. |
| 5,549,681 A | 8/1996 | Segmuller et al. |
| 5,782,926 A | 7/1998 | Lamprecht |
| 5,938,699 A | 8/1999 | Campbell |
| 5,951,604 A | 9/1999 | Scheker |
| 6,027,534 A | 2/2000 | Wack et al. |
| 6,051,751 A | 4/2000 | Sioshansi et al. |
| 6,059,832 A | 5/2000 | Menon |

(Continued)

OTHER PUBLICATIONS

Herbert, Timothy J., et al., "Disorders of the Distal Radio-Ulnar Joint and the Need for a New Ulnar Head Prosthesis", Martin, date unknown, pp. 1-23.

*Primary Examiner* — Thomas J Sweet
*Assistant Examiner* — Cheryl Miller
(74) *Attorney, Agent, or Firm* — Morgan, Lewis & Bockius LLP

(57) ABSTRACT

A sigmoid notch resurfacing prosthesis for application to the sigmoid notch of the distal radius. The sigmoid notch prosthesis generally includes a saddle and a radius portion for attachment to the distal radius. The saddle may be formed from ultra high molecular weight polyethylene or another durable self-lubricating material. The saddle includes an at least partially concave contoured depression having rounded edges that is securable to the radius portion. The saddle may be secured by a sliding notch snap fit design. The prosthesis may be adapted for articulation with the natural head of the ulnar or with an ulnar head prosthesis that has replaced the ulnar head.

29 Claims, 7 Drawing Sheets

U.S. PATENT DOCUMENTS

| | | | |
|---|---|---|---|
| 6,074,425 A | 6/2000 | Pappas | |
| 6,102,952 A * | 8/2000 | Koshino | 623/20.21 |
| 6,162,253 A | 12/2000 | Conzemius et al. | |
| 6,217,616 B1 | 4/2001 | Ogilvie | |
| 6,228,119 B1 * | 5/2001 | Ondrla et al. | 623/19.11 |
| 6,290,725 B1 | 9/2001 | Weiss et al. | |
| 6,302,915 B1 | 10/2001 | Cooney, III et al. | |
| 6,679,916 B1 * | 1/2004 | Frankle et al. | 623/19.12 |
| 6,709,459 B1 | 3/2004 | Cooney, III et al. | |
| 6,814,757 B2 | 11/2004 | Kopylov et al. | |
| 6,953,478 B2 * | 10/2005 | Bouttens et al. | 623/19.11 |
| 6,969,407 B2 | 11/2005 | Klotz et al. | |
| 7,160,331 B2 * | 1/2007 | Cooney et al. | 623/21.11 |
| 7,608,110 B2 * | 10/2009 | O'Driscoll et al. | 623/20.11 |
| 7,615,054 B1 * | 11/2009 | Bonutti | 606/88 |
| 2003/0135280 A1 | 7/2003 | Kopylov et al. | |
| 2004/0236428 A1 * | 11/2004 | Burkinshaw et al. | 623/20.15 |
| 2005/0049710 A1 | 3/2005 | O'Driscoll et al. | |
| 2006/0064173 A1 * | 3/2006 | Guederian | 623/20.11 |

* cited by examiner

SIGMOID NOTCH IMPLANT

STATEMENT OF RELATED APPLICATIONS

This application is a continuation of U.S. application Ser. No. 11/001,572, filed on Dec. 1, 2004 now U.S. Pat. No. 7,160,331 (allowed), which is hereby incorporated by reference in its entirety.

FIELD OF THE INVENTION

The present invention pertains generally to orthopedic prostheses. More particularly, the present invention pertains to a joint prosthesis for the distal radioulnar joint.

BACKGROUND OF THE INVENTION

The radius and ulna together form the bony structure of the forearm. The two bones articulate with one another at both their proximal and distal ends. The distal radioulnar joint is a "shallow socket" ball joint. The ulna, a relatively straight bone, translates dorsal-palmarly to accept the modestly bowed radius. The distal end of the radius articulates in pronation and supination on the distal head of the ulna at the sigmoid notch or fossa. The sigmoid notch socket in most wrists is relatively flat and a number of ligaments support the distal ulna where it meets the distal end of the radius. The supporting ligaments include the triangular fibrocartilage (TFC), the extensor carpi ulnaris (ECU) subsheath, and the ulnar collateral ligament complex. The stabilizing elements of the triangular fibrocartilage, the extensor carpi ulnaris subsheath, and the ulnar collateral complex work in cooperation with the distal ulna to transfer compressive loads between the ulnar carpus and the distal ulna across the distal radioulnar joint.

Unfortunately, fractures of the distal radius and other injuries of the forearm commonly occur and may cause rotational instability. Following these injuries to the forearm, ligament disruption, ulnar styloid fractures, and fractures into the distal radioulnar joint commonly occur. Fracture or dislocation involving the distal radioulnar joint often results in a loss of forearm rotation related to either instability or incongruity between the sigmoid fossa of the distal radius and the head of the ulna. A variety of different fractures involving the distal radius can cause this condition including the Colles' fracture and the Galeazzi fractures.

When there is loss of stability of the distal radioulnar joint, subsequent weakness in grip and pinch as well as potential loss of forearm rotation occur. Instability can also be associated with an injury to the triangular fibrocartilage or to the ulnar styloid. When instability is present, a number of ligament reconstructive procedures have been devised to assist in treating the unstable distal ulna. Unfortunately, ligament reconstruction of the distal ulna often does not restore complete stability and joint replacement is often performed in an effort to stabilize the joint.

Sometimes, when the distal ulna is damaged, the preferred treatment is hemiarthroplasty. That is to resect the head of the ulna and replace it with an ulnar head prosthesis which then is in contact with the natural bone of the radius. The prosthesis then articulates with the sigmoid notch to restore functionality to the distal radioulnar joint. Unfortunately, long term articulation between the man made implant and the natural bone may accelerate wear of the bone and lead to arthritic or degenerative change. This may cause the patient pain and restriction of motion.

In other circumstances, both the head of the ulna and the distal radius may suffer injury, arthritic change or degenerative change simultaneously. Then, it would be desirable to replace the articular surfaces of both the head of the uina and the sigmoid fossa. In addition, in some cases, replacement of the ulnar head with a prosthesis does not fully restore stability to the distal radioulnar joint. At present, patients that have had an ulnar head resection with implantation of an ulnar head prosthesis who still suffer from instability have few options.

In light of the foregoing, the surgical arts would benefit from access to a prosthetic device that could be used to restore the function of a damaged sigmoid notch articular surface. The surgical arts would also benefit from the availability of a prosthetic combination to repair an injured or degenerated distal radioulnar joint.

SUMMARY OF THE INVENTION

The invention solves many of the above referenced problems. The invention includes a sigmoid notch resurfacing prosthesis for application to the sigmoid notch of the distal radius. The sigmoid notch prosthesis generally includes a saddle and a radius portion for attachment to the distal radius. The saddle is securable to the radius portion and includes an articular surface having an at least partially concave contoured depression having rounded edges. The saddle may be secured by a sliding notch snap fit design or by other techniques known to those skilled in the art. The saddle may be formed from ultra high molecular weight polyethylene or another durable self-lubricating material for articulation with the head of an ulnar head implant. At this time, it is thought that metallic materials such as stainless steel or titanium are preferable for articulation with natural bone if the sigmoid notch implant is used as a hemiarthroplasty.

The invention may also include an ulnar head prosthesis for replacing the distal head of the ulna. The ulnar head prosthesis includes a head and a stem to replace the distal ulnar head. The prosthesis head is formed with a curved surface for articulation with the sigmoid notch prosthesis when installed. The head presents a bore to allow for attachment of the head to the stem. The head may be formed with suture holes for anchoring the head to soft tissues that are exposed after resection of the distal ulna.

The stem of the ulnar head prosthesis is elongated with an extended end for engaging within the intramedullary canal of the resected ulna. The stem of the ulnar head prosthesis also includes a distal end adapted for engagement with the bore in the head of the ulnar prosthesis. The stem further includes a collar between the proximal end of the stem and the distal end of the stem. The collar may be substantially flat. The proximal surface of the collar rests against the resected end of the distal ulna upon implantation to prevent the stem from penetrating excessively into the intramedullary canal of the ulna.

The saddle plate of the sigmoid notch implant includes a stem extending outwardly from a reverse side thereof as well as a countersunk screw receptacle for receiving a low profile spherical head bone screw. Interconnecting the screw receptacle and the stem is a stiffening rib. The opposite surface of the radius portion includes a substantially flat platform and a saddle retainer that surrounds the saddle on three sides and is grooved to receive a portion of the saddle thereunder to hold the saddle in place. In addition, the saddle retainer includes a retaining ridge so that the saddle can be slid onto the retaining structure and retained by a snap fit. The saddle and the saddle plate can also be connectable in other way known to those skilled in the art.

The sigmoid notch implant is implanted by first surgically accessing the distal radial ulnar joint. Once a surgeon decides the precise location for the sigmoid notch implant, the surgeon prepares the distal radius by drilling a hole to accept the stem of the saddle plate. A trial stem is placed in the hole in order to determine the proper location for pilot hole for a self-tapping bone screw. The trial stem has an undersized stem in order to preserve a press fit between the final implant and the bone of the distal radius.

Once the location of the pilot hole for the self-tapping bone screw is completed the surgeon burrs down the sigmoid notch to provide a flat buttress for the back of the saddle plate. The surgeon also burrs a small countersink to accept a collar surrounding the head of the spherical screw and the stiffening rib between the screw hole and the stem. The radius portion is then placed into the drill hole and impacted to seat it at its final location. Once the radius implant is successfully located, the self-tapping bone screw is placed in the pilot hole and tightened. Once the radius plate is fully seated, the head of the ulnar head implant is returned to its proper location at the head of the ulna.

In this embodiment, the saddle is inserted into the retaining structure of the radius plate and advance distally. Assuming the saddle is properly aligned with the radius plate, the saddle will move distally until it is about seventy five percent engaged, at which point it will rise up on a ramp in the bottom of the saddle as the ramp passes over the interference ridge on the surface of the radius plate. Once the saddle is completely seated in the saddle plate the surgeon reduces the joint and assesses range of motion. Assuming that relative motion of the ulnar head implant and the sigmoid notch implant is satisfactory, the surgeon repairs the joint capsule and closes the incision and the procedure is complete.

DETAILED DESCRIPTION OF THE INVENTION

Figure 18:
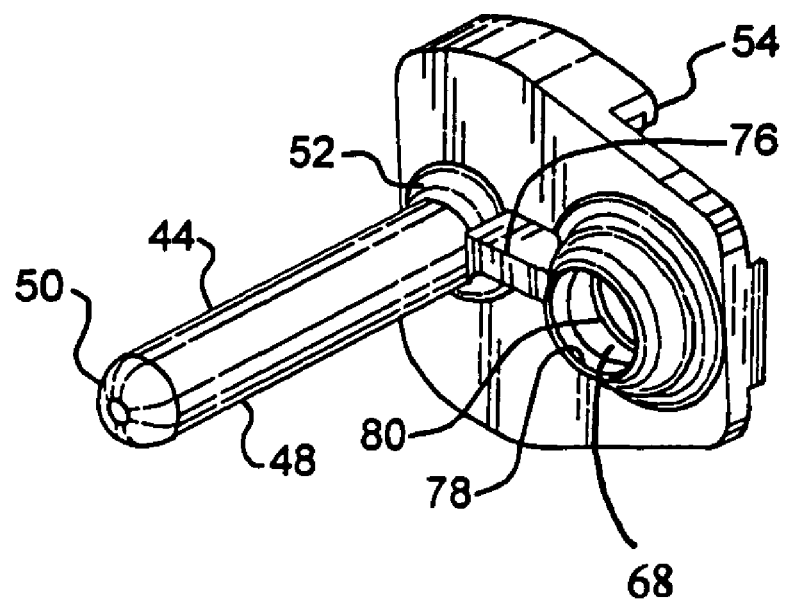
FIG. 18 is another perspective view of the radius component.
Figure 19:
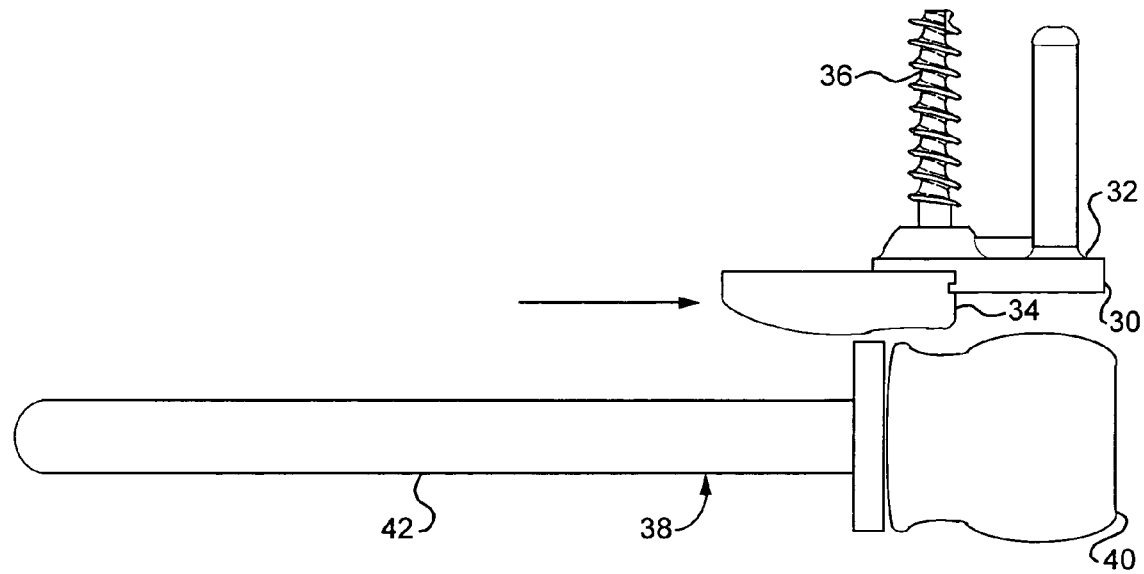
FIG. 19 is an elevational view of the sigmoid notch implant and an ulnar head implant with the saddle of the sigmoid notch implant partially installed.
Figure 20:
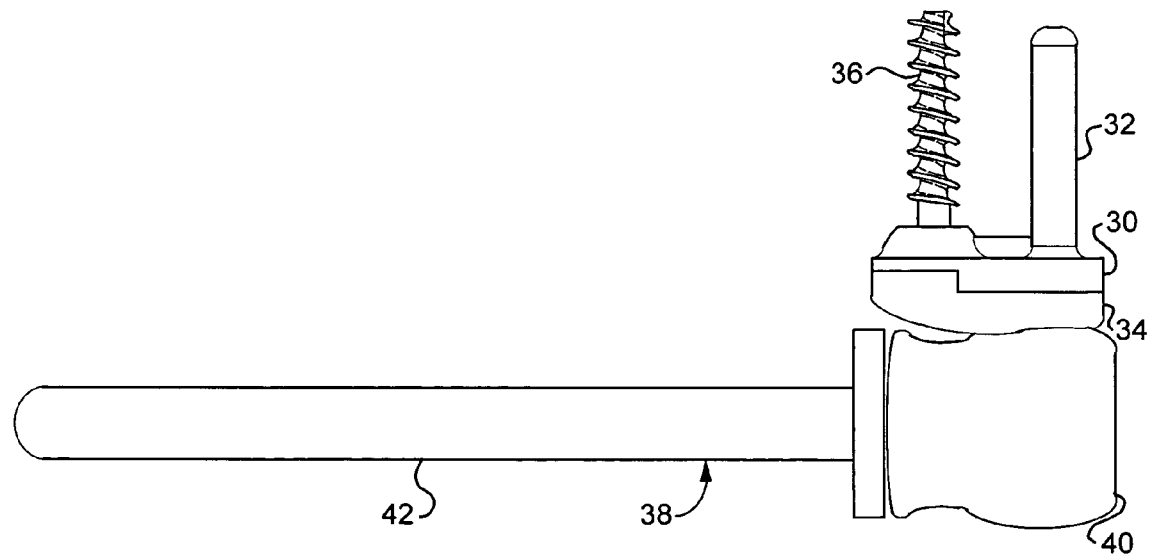
FIG. 20 is an elevational view of the sigmoid notch implant and an ulnar head implant with the saddle completely installed.

An embodiment of the sigmoid notch implant 30 generally includes radius portion 32, saddle 34 and bone screw 36: Referring to FIGS. 18 and 19 the sigmoid notch implant 30 is generally utilized along with an ulnar head implant 38. A typical ulnar head implant 38 includes a head portion 40 and a stem portion 42. One exemplary ulnar head prosthesis is disclosed in U.S. Pat. No. 6,302,915. The contents of that U.S. Patent are incorporated herein by reference.

Referring to FIGS. 1-6 and 13-18, radius portion 32 generally includes stem 44 and saddle plate 46. Stem 44 may extend outwardly from saddle plate 46 at a substantially right angle.

Stem 44 includes cylindrical portion 48 and rounded end 50. Stem 44 joins saddle plate 46 at fillet 52. Stem 44 may also have a tapered shape or include ridges or surface texturing thereon.

Referring to FIGS. 13-18 saddle plate 46 is roughly trapezoidally shaped and may be integrally formed with stem 44. Saddle plate 46 presents saddle retainer 54 and retainer ridge 56 on a side opposite from stem 44. Saddle plate 46 also defines screw hole 58 there through.

In one embodiment, saddle retainer 54 is structured to substantially surround saddle 34 on three sides. Saddle retainer 54 includes ridge 60 on three sides thereof, which together define a three-sided groove 62. Surface 64 of saddle plate 46 is substantially planar. Retaining ridge 56 extends upwardly from surface 64 at an end of saddle plate 46 substantially opposite from saddle retainer 54. Retaining ridge 56 may have a bevel 66 on the top thereof.

Screw hole 58 passes through saddle plate 46. Screw hole 58 desirably includes spherical countersink 68. As seen in FIGS. 14-16 and FIG. 18, screw hole 58 also passes through collar 70 which may be integrally formed with saddle plate 46 and which joins saddle plate 46 at circular fillet 74. Collar 70 is connected to stem 44 by stiffening rib 76 which interconnects circular fillet 74 with fillet 52. Stiffening rib 76 may also be integrally formed with saddle plate 46. Screw hole 58 may be located beneath saddle 34 when saddle 34 is assembled to saddle plate 46 or screw hole 58 may be in a location left exposed when saddle 34 is assembled to saddle plate 58.

Screw hole 58 defines cylindrical portion 78 on its inner aspect. Spherical countersink 68 defines circular bevel 80 where it meets surface 64.

Radius portion 32 is desirably machined, cast, molded or otherwise formed from a single piece of material. Radius portion 32 may be manufactured from implant grade 316L stainless steel or other biocompatible materials such as titanium. Biocompatible polymer or composite materials may be used as well.

Radius portion 32 may be mirror polished over surface 64, saddle retainer 54 and retaining ridge 56 and any other surfaces that do not make direct contact with the bone of the radius. The surfaces of stem 44, collar 70, stiffening rib 76, fillet 52 and circular fillet 74 and any other surface that makes contact with the bone of the radius may be roughened to encourage osseointegration such as by the application of commercially pure titanium plasma coating.

Saddle 34 presents articular portion 82 and securing portion 84. Referring to FIGS. 8-12, articular portion 82 presents articular face 85 which includes concave portion 86 and convex portion 88. Concave portion 86 and convex portion 88 are contoured so that articular face 85 substantially conforms to the shape of an ulnar head implant 38. Articular portion 82, desirably, has a radiused edge 90. Perimeter 92 of saddle 34 substantially conforms to the shape of the perimeter of saddle plate 46. The outline of saddle 34 is generally trapezoidal and includes rounded corners 94.

In an exemplary embodiment, concave portion 86 may be substantially spherical and have a radius of curvature of about 0.709 inches. Convex portion 88 may have a radius of curvature of about 0.5 inches. These values are exemplary and should not be considered limiting. Adjacent to convex portion 88 is sloped portion 96 which maybe sloped at about seventy degrees relative to the perimeter 92 of saddle 34. Saddle 34 can be adjusted in size, thickness and shape to conform to the natural head of the radius or to various ulnar head implants 38.

Securing portion 84 of saddle 34 presents bottom face 98 surrounded by tongue 100. Tongue 100 along with perimeter 92 define groove 102. Groove 102 extends substantially around perimeter 92 and is sized and structured to receive ridge 60 while tongue 100 fits into groove 62. Tongue 100 partially surrounds the edge of bottom face 98 on three sides. Tongue 100 extends outwardly from bottom face 98 and defines adjacent groove 102 which also extends around three sides of bottom face 98. Tongue 100 and groove 102 are dimensioned to mate with ridge 60 and groove 62 of saddle retainer 54.

Bottom face 98 is substantially planar and further presents recess 104. Recess 104 may be substantially rectangular in shape and includes flat portion 106 and sloped portion 108. Adjacent to recess 104 and beyond the edge of sloped portion 108 is retaining slot 110. Recess 104 is dimensioned so that flat portion 106 can receive retaining ridge 56 therein when tongue 100 and groove 102 are aligned with ridge 60 and groove 62 and saddle 34 is slidably engaged with saddle retainer 54. Retaining slot 110 is dimensioned to receive retaining ridge 56 therein when saddle 34 is slidably secured to radius portion 32. Note that saddle plate 46 and/or saddle 34 resiliently flex to make the engagement between retaining slot 110 and retaining ridge 56

Saddle 34 may be formed from ultra high molecular weight polyethylene or another self-lubricating material. Saddle 34 may also be from other polymers, composite or metallic material. It is generally believed that biocompatible metallic materials are preferred for articulation with the natural head of the ulna if the sigmoid notch implant 30 is used for hemiarthroplasty. It is specifically contemplated that saddle 34 may be joined to radius portion 32 by many other techniques as understood by those of ordinary skill in the art such as the use of screws, clamps or interference fit techniques.

Figure 1:
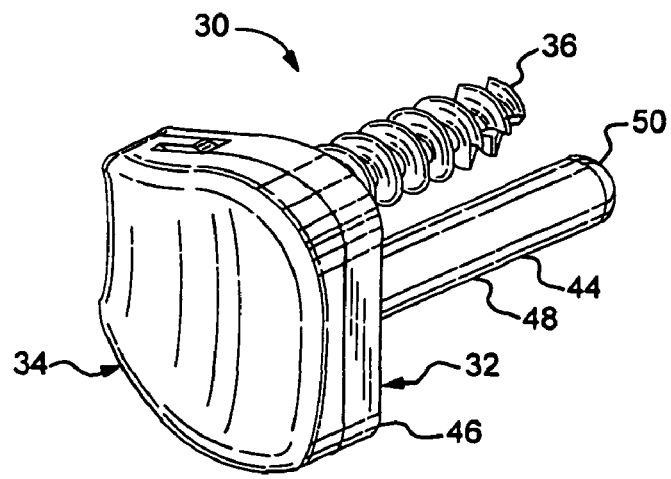
FIG. 1 is a perspective view of a sigmoid notch implant in accordance with the present invention.
Figure 2:
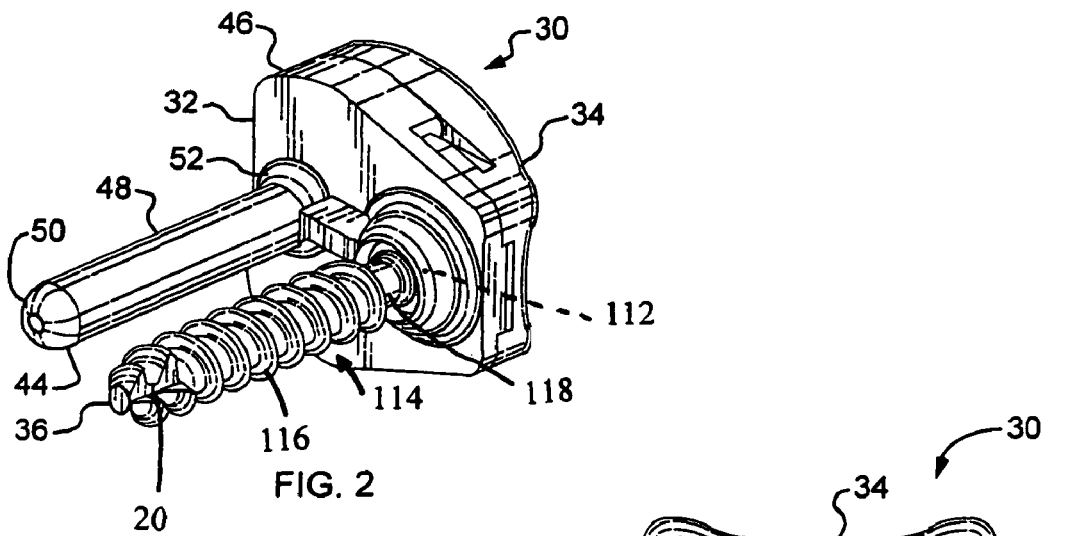
FIG. 2 is another perspective view of the sigmoid notch implant.
Figure 3:
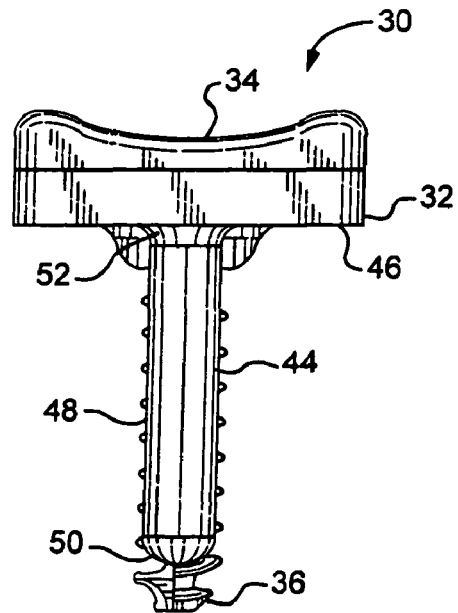
FIG. 3 is a front elevational view of the sigmoid notch implant.
Figure 4:
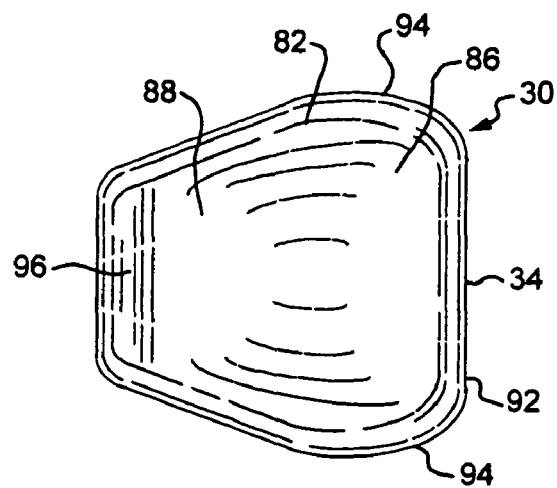
FIG. 4 is a plan view of the sigmoid notch implant.
Figure 5:
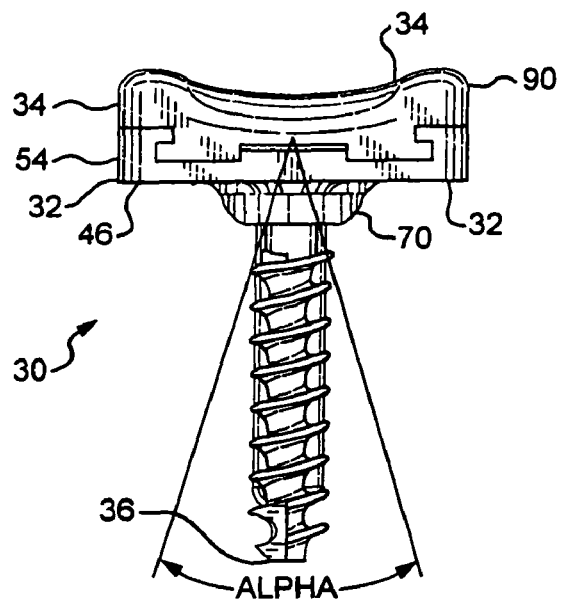
FIG. 5 is a rear elevational view of the sigmoid notch implant.
Figure 6:
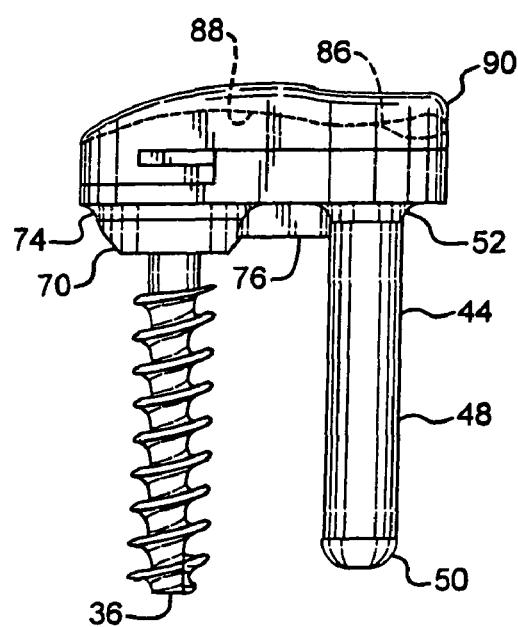
FIG. 6 is a side elevational view of the sigmoid notch implant.
Figure 7:
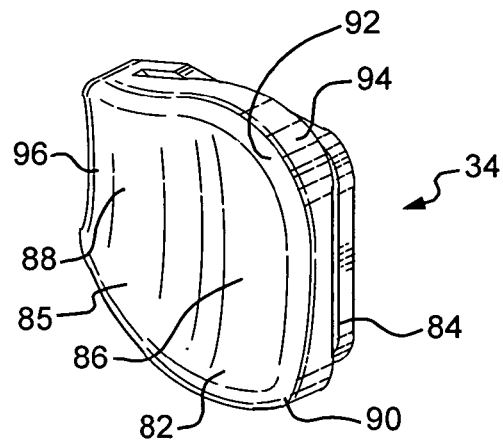
FIG. 7 is a perspective view of a saddle in accordance with the present invention.
Figure 8:
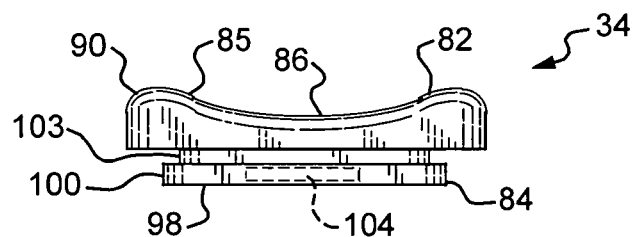
FIG. 8 is a front elevational view of the saddle in accordance with the present invention.
Figure 9:
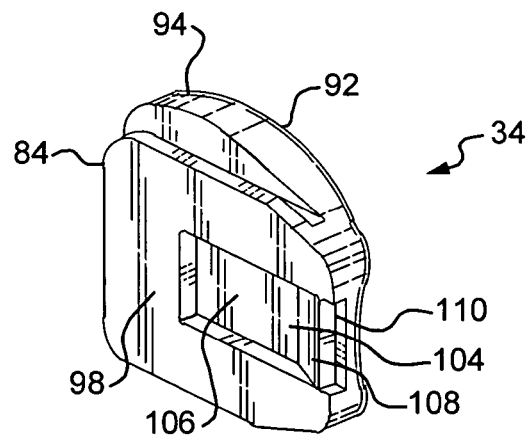
FIG. 9 is a perspective view of the saddle in accordance with the present invention.
Figure 10:
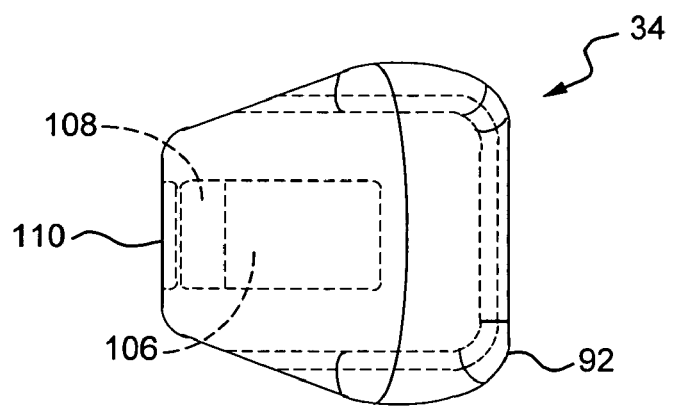
FIG. 10 is a plan view of the saddle with phantom lines showing internal structures.
Figure 11:
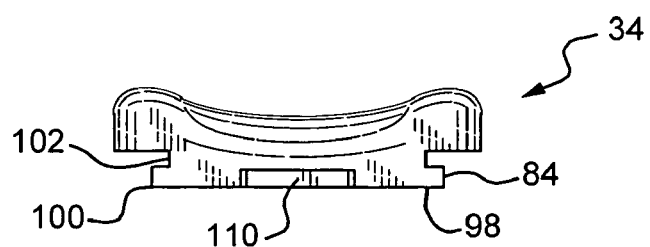
FIG. 11 is a rear elevational view of the saddle.
Figure 12:
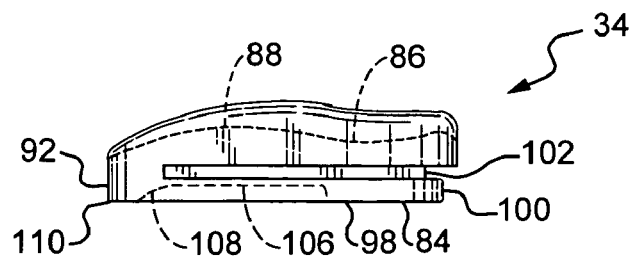
FIG. 12 is a side elevational view of the saddle with phantom lines depicting internal structures.
Figure 13:
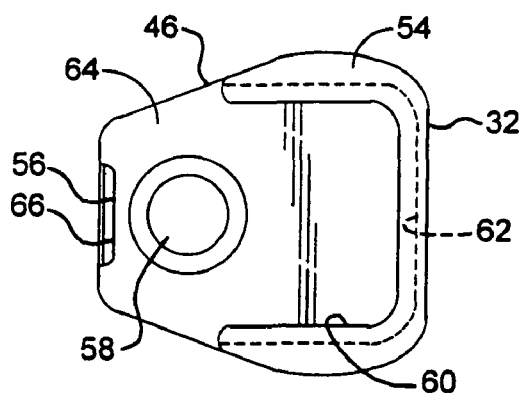
FIG. 13 is a plan view of a radius component of the sigmoid notch implant.
Figure 14:
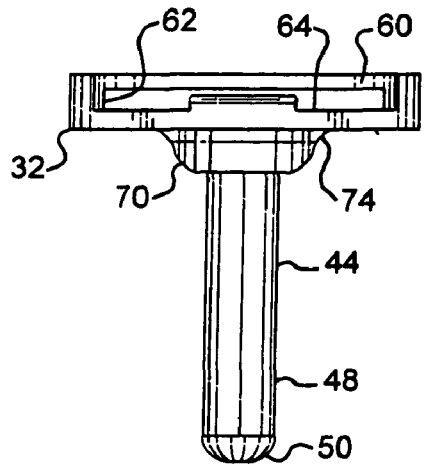
FIG. 14 is a front elevational view of the radius component.
Figure 15:
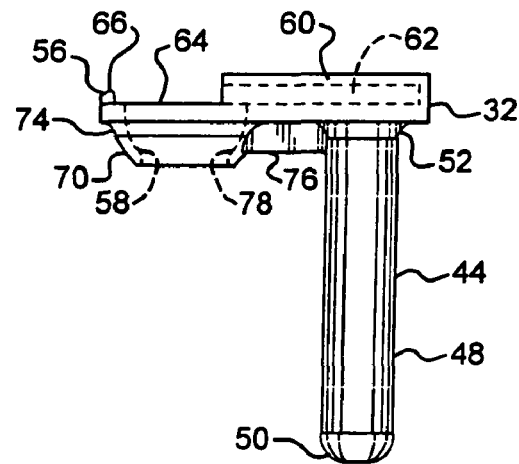
FIG. 15 is a side elevational view of the radius component.
Figure 16:
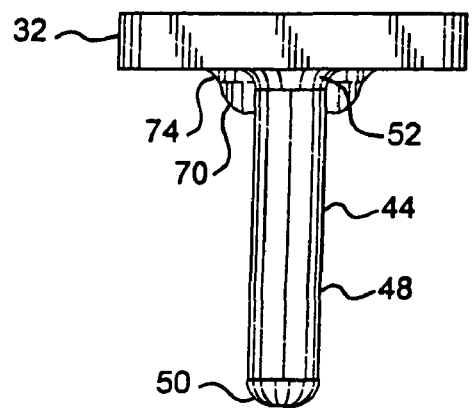
FIG. 16 is a rear elevational view of the radius component.
Figure 17:
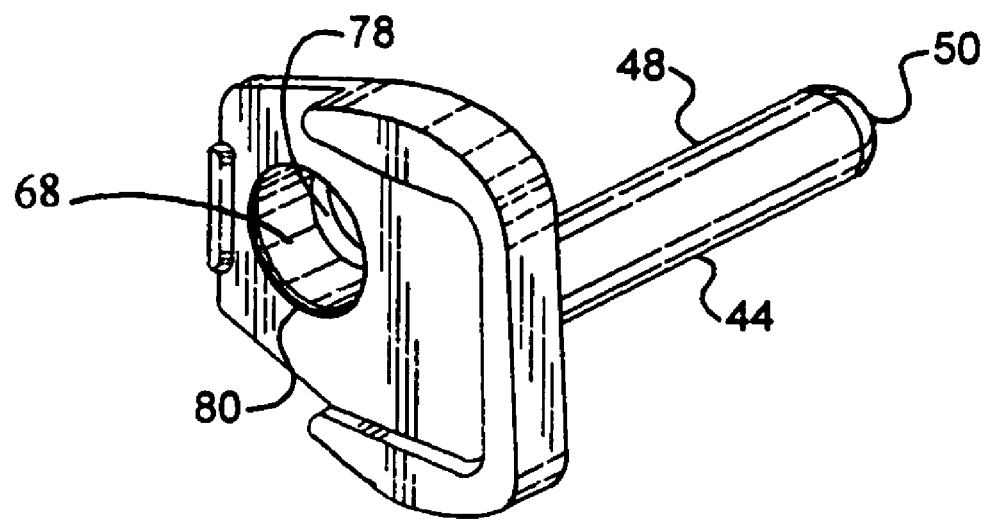
FIG. 17 is a perspective view of the radius component.

Bone screw 36 is a spherical head bone screw. Bone screw 36 includes spherical head 112 and shaft 114. Shaft includes threaded portion 116 and unthreaded portion 118. Bone screw 36 desirably includes flutes 20 to facilitate a self-threading design. Bone screw 36 may be manufactured to the standards of ISO 5835. Referring to FIG. 5, bone screw 36 may angulate in a conical fashion at an angle alpha within spherical countersink 68. For example, bone screw 36 may articulate conically at a solid angle alpha of about thirty degrees.

In operation, sigmoid notch implant 30 articulates with ulnar head implant 38 to restore stability and pain free natural motion to the distal radial ulnar joint. To implant sigmoid notch implant 30 the surgeon first exposes the distal radial ulnar joint. In this discussion of the implantation of sigmoid notch implant 30 it will be assumed that an ulnar head implant 38 having a metallic articular surface has already been implanted to replace the head of the ulna. It is specifically contemplated that sigmoid notch implant 30 may also be implanted to articulate with the natural head of the ulna as a hemiarthroplasty. If this aspect of the invention is practiced it is to be understood that saddle 34 may be formed of a metallic material or another biocompatible material appropriate to articulate with living bone. At this time, it is generally thought that for two surface arthroplasty a metal to polymer interface is preferred and for hemiarthroplasty a metallic to bone interface is preferred but these beliefs should not be considered to be limiting.

Once the joint is exposed the surgeon removes the head portion 40 of the ulnar head implant 38 and sets it aside. First however, the surgeon measures from the distal face of the existing ulnar head implant 38 to determine the location for drilling a hole to accept the stem 44 of radius portion 32. The surgeon should estimate the drilled depth required to accept stem 44. The surgeon then drills a hole in the distal radius utilizing, for example, a 3.5-millimeter drill.

Once the hole to receive stem 44 is drilled the surgeon will use a trial radius portion (not shown) which has an undersized trial stem to preserve a press fit for the sigmoid notch implant 30. Once the trial implant is satisfactorily placed in the drilled hole the surgeon drills a pilot hole for the self-tapping bone screw 36 using an appropriately sized drill. The pilot hole is located so that the pilot hole is substantially centered in screw hole 58. The pilot hole may be angled for optimal placement of bone screw 35. The pilot hole may be angled as needed to avoid pre-existing implant hardware, or to assist in fracture fixation or to avoid fractured portions of the bone. If the pilot hole is drilled non-parallel to the hole to receive stem 44 axial pullout strength is increased.

Once the pilot hole for bone screw 36 is made, the surgeon removed the trial radius portion and burrs down the sigmoid notch to provide a flat buttress for saddle plate 46. The surgeon also burrs a small countersink to receive collar 70 and a space to receive stiffening rib 76.

The surgeon places radius portion 32 of sigmoid notch implant 30 so that stem 44 is in the drilled hole. The surgeon then impacts radius portion 32 until it is secured by press fit in the predrilled hole by stem 44 and flush against the flat buttress surface of the radius. If the hole is too small to receive stem 44, the surgeon should consider removing radius portion 32 and redrilling to remove debris rather than applying excessive force to radius portion 32 in an effort to insert it.

Once radius portion 32 is in place, bone screw 36 is inserted and tightened. It is important that bone screw 36 be tightened evenly and that saddle plate 46 be evenly supported against the radius to avoid bending saddle plate 46. In addition, care should be taken to protect the polished surfaces of the ulnar head implant 38 and the radius portion 32 (for example by handling head portion 40 carefully). Any scratches on the polished surfaces of the ulnar head implant 38 may decrease the wear life of saddle 34. Scratches on portions of the components that articulate with surrounding tissues may encourage inflammation.

Referring to FIGS. 18 and 19, the surgeon slides saddle 34 (of UHMWPE or other polymer material) into radius portion 32 so that tongue 100 and groove 102 mate with groove 62 and ridge 60. When the saddle 34 is about 75 percent engaged sloped portion 96 of saddle 34 will engage bevel 66 of retaining ridge 56. If need be, the surgeon can stake an osteotome into the radius and pry against saddle 34 to overcome the resistance of retaining ridge 56 against sloped portion 108.

Once saddle 34 snaps into place in saddle retainer 54 implantation of the sigmoid notch implant 30 is complete.

The surgeon then replaces the head portion 40 of ulnar head implant 38 and reduces the joint to assess range of motion. Assuming that range of motion and alignment is acceptable, the surgeon repairs the joint capsule and closes the skin.

If the invention is practiced as a hemiarthroplasty, saddle may be formed of metallic material and be secured to radius portion 32 by another technique as discussed above. In a hemiarthroplasty, the head of the ulna will, of course remain intact.

The present invention may be embodied in other specific forms without departing from the central attributes thereof, therefore, the illustrated embodiments should be considered in all respects as illustrative and not restrictive, reference being made to the appended claims rather than the foregoing description to indicate the scope of the invention.

What is claimed is:

1. An orthopedic prosthesis sized and configured for implantation at the distal radioulnar joint, the prosthesis comprising:
    a radius portion adapted to be securable to the distal radius in the vicinity of the sigmoid fossa, the radius portion including a plate presenting a hole extending completely through the plate, a stem integral with and extending outwardly from the plate, and a collar surrounding the hole; and
    a saddle including an articular face configured for facing an ulna, the articular face having a partially concave, partially convex surface capable of articulating with the ulna or a prosthesis that has replaced a head of the ulna, the saddle being mechanically securable to the radius portion.

2. The prosthesis as claimed in claim 1, in which the radius portion comprises a saddle retainer to secure the saddle to the radius portion.

3. The prosthesis as claimed in claim 1, further comprising a bone screw that is articulable with the radius portion to be angularly adjustable relative to the radius portion.

4. The prosthesis as claimed in claim 1, in which the saddle is formed of a polymer and the saddle is shaped to conform to an ulnar head implant that has replaced the natural ulnar head.

5. The prosthesis as claimed in claim 1, in which the plate comprises a saddle retainer portion located at a perimeter of the plate and surrounding at least a portion of three sides of the plate.

6. The prosthesis as claimed in claim 1, in which the articular face comprises a sloped portion.

7. The prosthesis as claimed in claim 1, in which the saddle is secured to the radius portion by a tongue and groove interface.

8. The prosthesis as claimed in claim 1, in which at least a portion of the prosthesis expected to be in contact with bone is roughened to encourage osseointegration.

9. The prosthesis as claimed in claim 1, in which at least a portion of the prosthesis is titanium plasma coated.

10. The prosthesis of claim 1, further comprising a stiffening rib between the stem and the collar.

11. An orthopedic prosthesis for implantation at the distal radioulnar joint, the prosthesis comprising:
    a radius portion adapted to be securable to the distal radius in the vicinity of the sigmoid fossa, the radius portion including a plate presenting a hole therethrough and a stem integral with and extending outwardly from the plate, wherein the plate is substantially trapezoidal in shape; and
    a saddle including an articular face configured for facing an ulna, the articular face having a partially concave, partially convex surface capable of articulating with the ulna or a prosthesis that has replaced a head of the ulna, the saddle being mechanically securable to the radius portion.

12. The prosthesis as claimed in claim 11, further comprising a collar surrounding the hole.

13. The prosthesis as claimed in claim 12, further comprising a stiffening rib between the stem and the collar.

14. A prosthesis for implantation at the distal radioulnar joint comprising:
    a plate having a stem extending outwardly from a first side of the plate, a retainer disposed on a second side of the plate, a plate groove defined by the retainer, a hole extending from the first side of the plate to the second side of the plate, and a collar disposed on the first side around the hole; and
    a saddle including:
        a first side having a face with a concave portion and a convex portion; and
        a second side having a tongue configured to be received in the plate groove and a tongue groove defined by the tongue configured to receive the retainer when the saddle is engaged with the plate.

15. The prosthesis of claim 14, wherein the hole is configured to permit conical articulation of a bone screw received therein with the plate.

16. The prosthesis of claim 14, wherein the hole includes a spherical countersink.

17. The prosthesis of claim 14, wherein the face is contoured to conform to the shape of an ulnar head implant.

18. The prosthesis of claim 14, wherein the concave portion has a substantially spherical curvature.

19. The prosthesis of claim 14, wherein the face includes a radiused edge.

20. The prosthesis of claim 14, wherein the saddle includes a perimeter substantially conforming to a perimeter of the plate.

21. The prosthesis of claim 14, wherein the tongue groove extends substantially around a perimeter of the saddle.

22. The prosthesis of claim 14, wherein the second side of the saddle includes a bottom face defining a recess.

23. The prosthesis of claim 22, wherein the recess includes a flat portion and a sloped portion.

24. The prosthesis of claim 22, wherein the second side of the plate further includes a ridge configured to be received in the recess.

25. The prosthesis of claim 14, further comprising a stiffening rib between the stem and the collar.

26. A prosthesis for implantation at the distal radioulnar joint comprising:
    a plate having a stem extending outwardly from a first side of the plate, a retainer disposed on a second side of the plate, a plate groove defined by the retainer, and a hole extending from the first side of the plate to the second side of the plate;
    a saddle including:
        a first side having a face with a concave portion and a convex portion; and
        a second side having a tongue configured to be received in the plate groove and a tongue groove defined by the tongue configured to receive the retainer when the saddle is engaged with the plate; and
    an ulnar implant for replacement of the distal head of an ulna bone including a head having a curved surface configured to articulate with the face, wherein the face is contoured to substantially conform to the shape of the head.

27. The prosthesis of claim 26, wherein the plate further includes a collar disposed on the first side around the hole.

28. The prosthesis of claim 27, wherein the plate further includes a stiffening rib between the collar and the stem.

29. The prosthesis of claim of claim 26, wherein the ulnar implant further includes an elongate stem attached to the head configured for engagement within the intramedullary canal of the ulna bone.

* * * * *